US00PP11055P

United States Patent [19]

Flemer, III

[11] Patent Number: Plant 11,055

[45] Date of Patent: Sep. 7, 1999

[54] FORSYTHIA HYBRID PLANT NAMED 'PRINCETON GOLD'

[75] Inventor: William Flemer, III, Plainsboro Township, Middlesex County, N.J.

[73] Assignee: Treesearch, Allentown, N.J.

[21] Appl. No.: 08/916,388

[22] Filed: Aug. 22, 1997

[51] Int. Cl.[6] ..... A01H 5/00

[52] U.S. Cl. ..... Plt./230

[58] Field of Search ..... Plt./54.1, 230

*Primary Examiner*—Howard J. Locker
*Assistant Examiner*—Melissa L. Kimball
*Attorney, Agent, or Firm*—James A. Lucas

[57] ABSTRACT

A new and distinct Forsythia variety characterized by the very large size of the flowers which have a rich golden color and with much broader petals than any other Forysthia variety known to me. The flowers are very dense on the twigs so that the shrub is a solid mass of gold when in bloom. It forms a dense, rounded shrub, broader than tall. The flower buds survive cold winter in USDA hardiness zone 5-A when the flower buds of *Forsythia intermedia* varieties have been killed.

2 Drawing Sheets

BACKGROUND OF THE INVENTION

This invention relates to Forsythia and primarily to a Forsythia hybrid which is a product of crossing an unpatented seed parent *Forsythia intermedia* 'Spectabilis' with an unpatented pollen parent *Forsythia ovata* 'Tetra Gold '.

I selected the plant of this application from a row of *Forsythia intermedia* 'Spectabilis' seedlings in a nursery located near Plainesboro Township, N.J. I asexually reproduced the plant by soft wood cuttings in a cultivated area at the nursery, have observed the plants thus produced, and find that the characteristics initially observed are in fact reproduced in successive generations.

Forsythias are popular plants due to their bright and colorful yellow flowers which appear in the spring prior to the leaves. They are fast growing opposite-leaved shrubs easily propagated by hard or soft wood cuttings. *Forsythia intermedia* originated as a hybrid species in Europe (*F. suspensa*×*F. viridissima*). It is characterized by being sturdy and upright with sloghtly arching branches. The seed parent, *Fosythia intermedia* 'Spectabilis' is one of the most popular Forsythias having flowers produced in large quantities and clusters while retaining the upright and sturdy character of *F. intermedia.* The flowers are large and have a dark vivid yellow color. *F. ovata* is characterized by having small, erratically produced flowers. The flowers, though, are hardier than other Forsythias. Becasue of its hardiness *F. ovata* varieties, like 'Tetra Gold', are planted in colder areas where the flower buds can withstand the winter cold.

BRIEF SUMMARY OF THE INVENTION

The plant of this invention is characterized by having traits of each parent. It is remarkable for the very large size of the flowers of a rich golden color, and unusually broad petals for a Forsythia plant. The flowers are very dense on the twigs so that the shrub is a solid mass of gold when in bloom. It forms a dense, rounded shrub, broader than tall. The flower buds survive cold winter in USDA hardiness zone 5 when the flower buds of *Forsythia intermedia* varieties have been killed.

DESCRIPTION OF THE DRAWINGS

This new variety of Forsythia is illustrated by accompanying photographic drawings and depicts the plant by the best possible color representation using color photography.

BOTANICAL DESCRIPTION OF THE PLANT

Figure 1:
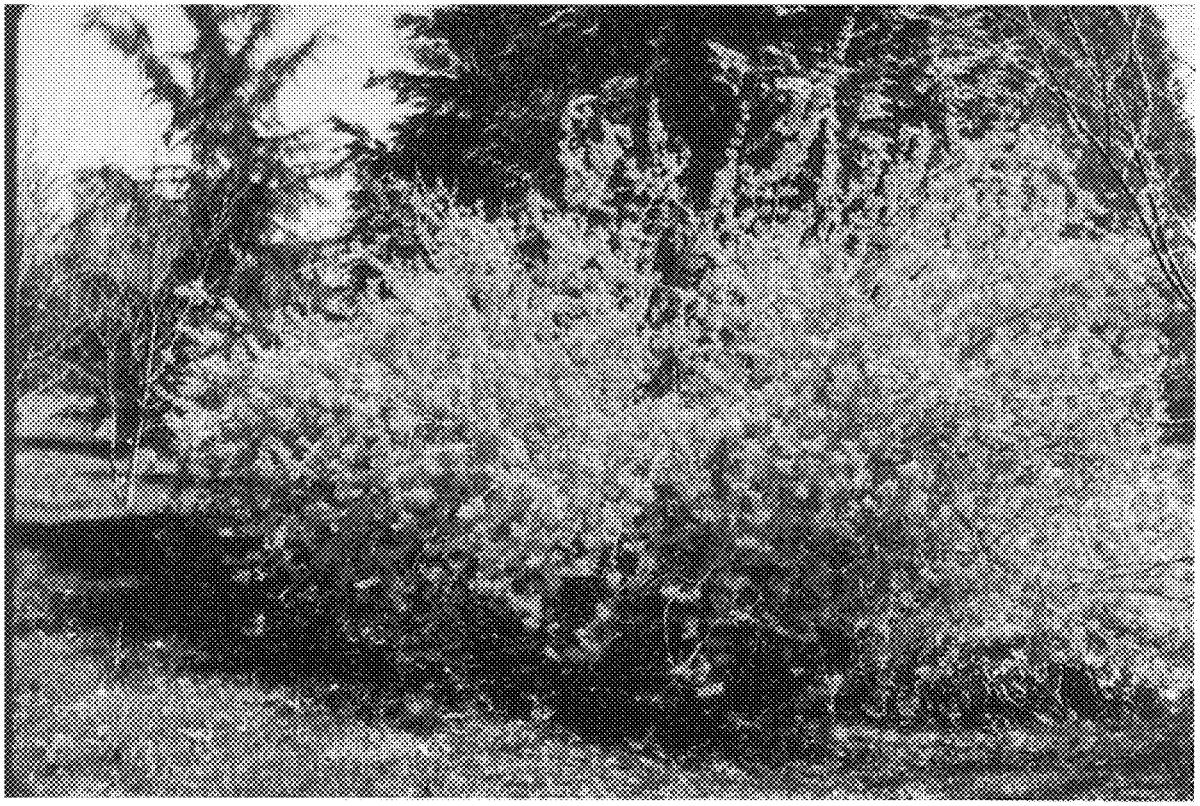
FIG. 1 is a view showing the entire shrub.
Figure 2:
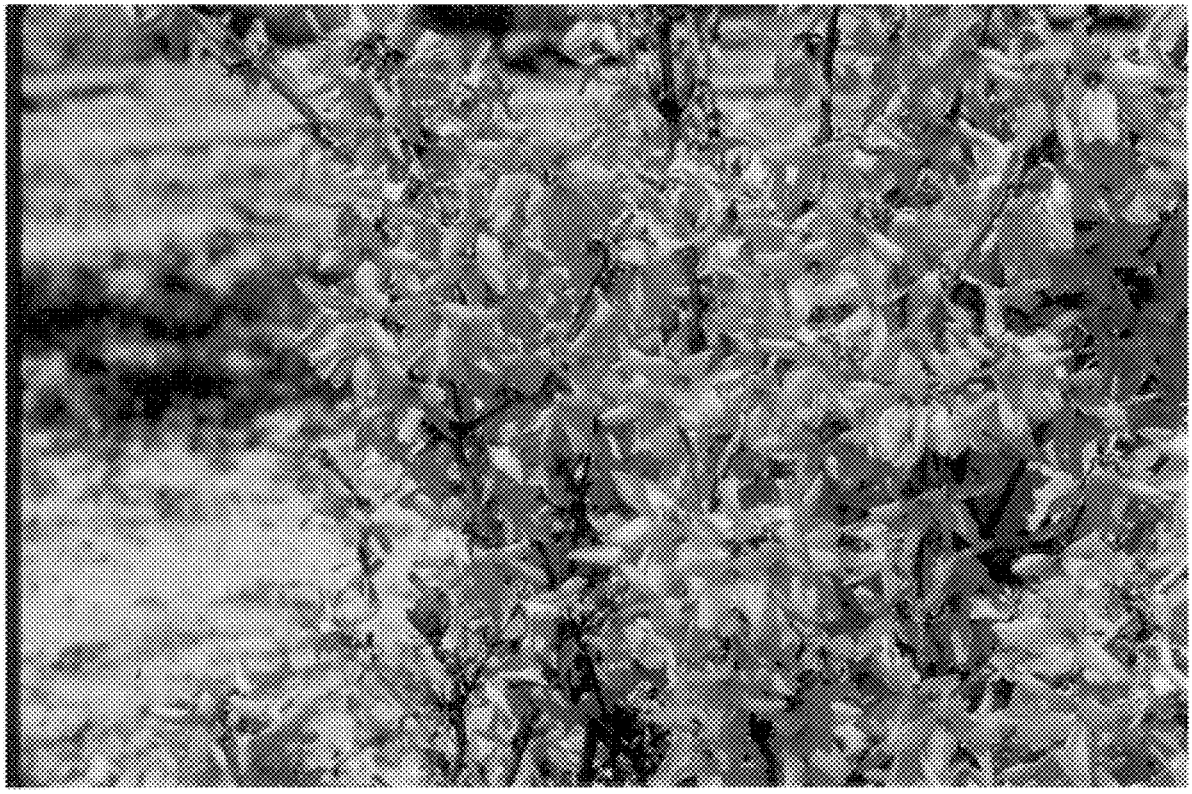
FIG. 2 is a view showing a close-up of the flowers and twigs.

The details which formed the basis for this description were observed at a nursery in Plainsboro Twp. N.J. in 1987. All color references below are measured against the Munsell Color Chart. Colors are approximate as color depends on horticultural practices such as light level and fertilization rate, among others.

Parentage:
- *Seed parent.*—*Forsythia intermedia* 'Spectabilis'.
- *Pollen plant.*—*Forsythia ovata* 'Tetra Gold'.

Tree: Shrub.
- *Overall appearance.*—Spreading; dense and hardy.
- *Size.*—Large, 2 meters high by 3 meters wide.

Trunk: Stocky.
- *Color.*—Moderate yellowish brown, 10YR 4/4.

Branches: Abundant; stocky and smooth.
- *Angle.*—35°–45°.
- *Color.*—Moderate yellowish brown, 10 YR 4/4.
- *Lenticels.*—Moderately abundant. Number — 3 per cm of twig length.
- *Color.*—Dark Orange Yellow 10 YR 6/8.

Leaves:
- *Quantity.*—Abundant.
- *Arrangement.*—Opposite, borne in pairs.
- *Length.*—8 cm.
- *Width.*—3 cm.
- *Shape.*—Oblong, lanceolate.
- *Color.*—Upper surface, dark yellowish green, 10 GY 4/5. Lower surface, moderate yellow green 5 GY 5/6.
- *Margin.*—Serrate on terminal ⅓ of the leaf.
- *Petiole.*—Short, 1.5 cm long.
- *Glands.*—None.
- *Stipules.*—None.

Flower buds:
- *Hardiness.*—Very hardy, Zone 5-A.
- *Size.*—1 cm long.
- *Shape.*—Narrow, pointed and borne in opposite clusters on the branches.
- *Color.*—Strong yellowish brown 10 YR 5/0.

Flowers: Borne in opposite 2 to 4 flowered clusters.

*Dates first bloom*—April 1; Full bloom — April 10.

*Quantity.*—Very abundant.

*Size.*—Very large-5 cm in diameter by 2 cm high.

*Lastingness on plant.*—2 weeks in central New Jersey.

*Fragrance.*—None observed.

Petalage:

*Number of petals.*—4.

*Shape of petals.*—Ovate, with square, slightly toothed tips.

*Size of petals.*—Very large.

*Length.*—3 cm.

*Width.*—1.1 cm.

*Color.*—Vivid yellow 2.5Y 8/12, base of petals 10 YR 8/10.

Fruits: None observed.

Reproductive organs:

*Stamen.*—Anthers — Few and small. Color — Moderate Orange Yellow 10YR8/10. Arrangement-Inserted at the base of the calyx. Filaments: Threads — Short (0.5 cm. long). Color — Vivid greenish yellow 7.5Y8/12. Pollen: Color — Moderate orange yellow 7.5 YR8/8. Styles: Slender, with 2-lobed stigma. Length — Short (0.4 cm. long) and thin. Stigma: 2-lobed. Color — Brilliant greenish yellow 7.5Y 9/8.

*Ovaries.*—All enclosed in calyx.

Disease: No unusual susceptibility to known diseases observed to date.

I claim:

1. A new and distinct Forsythia plant, substantially as herein shown and described, characterized particularly as to novelty by its very large flowers of a rich golden color with broad petals forming a dense, rounded shrub, broader than tall, and by its hardy flower buds able to survive cold winter in USDA hardiness zone 5.

* * * * *